United States Patent

Wuerzer

Patent Number: 4,473,392
Date of Patent: Sep. 25, 1984

[54] HERBICIDAL AGENTS BASED ON DIPHENYL ETHERS AND BENZOTHIADIAZINONE DIOXIDES OR PYRIDINOTHIADIAZINONE DIOXIDES, AND THE USE THEREOF

[75] Inventor: Bruno Wuerzer, Otterstadt, Fed. Rep. of Germany

[73] Assignee: BASF Aktiengesellschaft, Fed. Rep. of Germany

[21] Appl. No.: 366,186

[22] Filed: Apr. 7, 1982

Related U.S. Application Data

[63] Continuation of Ser. No. 190,900, Sep. 25, 1980, abandoned.

[30] Foreign Application Priority Data

Oct. 8, 1979 [DE] Fed. Rep. of Germany ........ 2940698

[51] Int. Cl.³ ............................................ A01N 43/88
[52] U.S. Cl. ............................................ 71/91; 71/98
[58] Field of Search ............................................ 71/91

[56] References Cited

FOREIGN PATENT DOCUMENTS 1542836 4/1971 Fed. Rep. of Germany .
7721320 8/1975 Japan .

OTHER PUBLICATIONS

Frost et al., Chem. Abst. vol. 85, (1976) 15198z.

Primary Examiner—Catherine L. Mills
Attorney, Agent, or Firm—Keil & Weinkauf

[57] ABSTRACT

Herbicidal agents containing a composition of a diphenyl ether of the formula

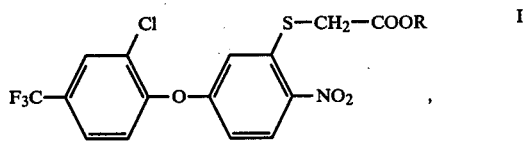

where R is hydrogen, a cation, alkyl or haloalkyl of from 1 to 4 carbon atoms, and a substituted thiadiazin-4(3)-one-2,2-dioxide of the formula

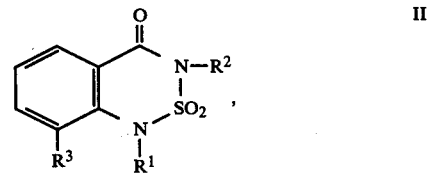

where $R^1$ is hydrogen, a cation, cyano or alkoxyalkyl of from 2 to 4 carbon atoms, $R^2$ is alkyl of from 1 to 4 carbon atoms and $R^3$ is hydrogen, alkyl of from 1 to 4 carbon atoms or halogen, or of the formula

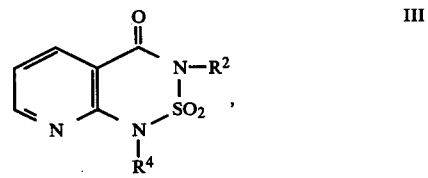

where $R^4$ is hydrogen or a cation and $R^2$ is alkyl of from 1 to 4 carbon atoms.

4 Claims, No Drawings

HERBICIDAL AGENTS BASED ON DIPHENYL ETHERS AND BENZOTHIADIAZINONE DIOXIDES OR PYRIDINOTHIADIAZINONE DIOXIDES, AND THE USE THEREOF

This is a continuation of application Ser. No. 190,900, filed Sept. 25, 1980, now abandoned.

The present invention relates to herbicidal agents containing compositions of substituted diphenyl ethers and 1H-2,1,3-benzothiadiazin-4(3H)-one-2,2-dioxides or 1-H-pyridino-[3.2-e]-2,1,3-thiadiazin-4(3H)-one-2,2-dioxides, and processes for combating unwanted plant growth with these herbicidal agents.

Substituted diphenyl ethers as herbicidal active ingredients have been disclosed (Japanese Publication No. 77/21320). Although they are already highly effective at low application rates, they cause damage to cereals and other crop plants.

It has also been disclosed that 3-alkyl-1H-2,1,3-benzothiadiazin-4(3H)-one-2,2-dioxides and 1H-pyridino-[3.2-e]-2,1,3-thiadiazin-4(3H)-one-2,2-dioxides are suitable for the selective control of unwanted broadleaved plants (German No. 1,542,836, German Laid-Open Applications DE-OS No. 2,656,289, DE-OS No. 2,430,353, DE-OS No. 2,444,383, DE-OS No. 2,553,209 and DE-OS No. 2,443,901).

I have found that herbicidal agents containing a composition of a diphenyl ether of the formula

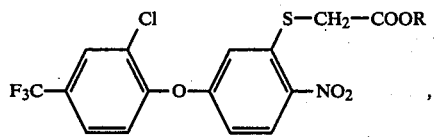

where R is hydrogen, a cation, alkyl or haloalkyl of from 1 to 4 carbon atoms, and a substituted 1H-2,1,3-benzothiadiazin-4(3H)-one-2,2-dioxide of the formula

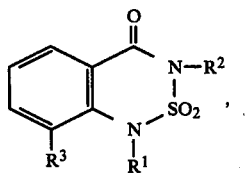

where $R^1$ is hydrogen, a cation, cyano or alkoxyalkyl of from 2 to 4 carbon atoms, $R^2$ is alkyl of from 1 to 4 carbon atoms and $R^3$ is hydrogen, alkyl of from 1 to 4 carbon atoms or halogen, or a substituted 1H-pyridino-[3.2-e]-2,1,3-thiadiazin-4(3H)-2,2-dioxide of the formula

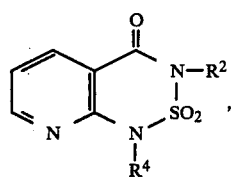

where $R^4$ is hydrogen or a cation and $R^2$ is alkyl of from 1 to 4 carbon atoms, have a more intensive action on broadleaved plants than herbicidal agents containing as active ingredients only substituted diphenyl ethers of the formula I, or only benzothiadiazinone dioxides of the formula II or pyridinothiadiazinone dioxides of the formula III. Surprisingly, the compositions of diphenyl ethers of the formula I and benzothiadiazinone dioxides of the formula II or pyridinothiadiazinone dioxides of the formula III have a synergistic action. It is also surprising that these compositions are tolerated by crop plants better than herbicidal agents containing diphenyl ethers of the formula I alone as active ingredients.

Examples of diphenyl ethers of the formula I in the agents according to the invention are 2-chloro-4-trifluoromethyl-3'-ethoxycarbonylmethylthio-4'-nitrodiphenyl ether and 2-chloro-4-trifluoromethyl-3'-hydroxycarbonyl-methylthio-4'-nitrodiphenyl ether or its sodium salt.

Examples of benzothiadizinone dioxides of the formula II in the agents according to the invention are 3-isopropyl-1H-2,1,3-benzothiadiazin-4(3H)-one-2,2-dioxide, 3-isopropyl-8-chloro-1H-2,1,3-benzothiadiazin-4(3H)-one-2,2-dioxide, 3-isopropyl-8-fluoro-1H-2,1,3-benzothiadiazin-4(3H)-one-2,2-dioxide, 3-(1-methylethyl)-8-methyl-1H-2,1,3-benzothiadiazin-4(3H)-one-2,2-dioxide, and salts of these compounds, suitable salts being substituted or unsubstituted ammonium salts, such as the dimethylammonium or diethanolammonium salt, or metal salts, such as alkali metal salts, e.g., the sodium salt, 1-methoxymethyl-3-isopropyl-2,1,3-benzothiadiazin-4(3H)-one-2,2-dioxide, 1-methoxymethyl-8-chloro-3-isopropyl-2,1,3-benzothiadiazin-4(3H)-one-2,2-dioxide, 1-methoxymethyl-8-fluoro-3-isopropyl-2,1,3-benzothiadiazin-4(3H)-one-2,2-dioxide, 1-cyano-8-chloro-3-isopropyl-2,1,3-benzothiadiazin-4(3H)-one-2,2-dioxide, 1-cyano-8-fluoro-3-isopropyl-2,1,3-benzothiadiazin-4(3H)-one-2,2-dioxide, 1-cyano-8-methyl-3-isopropyl-2,1,3-benzothiadiazin-4(3H)-one-2,2-dioxide and 1-cyano-3-isopropyl-2,1,3-benzothiadiazin-4(3H)-one-2,2-dioxide.

Examples of pyridinothiadiazinone dioxides of the formula III in the agents according to the invention are 3-isopropyl-1H-pyridino-[3.2-e]-2,1,3-thiadiazin-4(3H)-one-2,2-dioxide and salts thereof, e.g., alkali metal salts, such as the sodium and potassium salts, and substituted or unsubstituted ammonium salts, such as the dimethylammonium salt.

Particularly preferred composition components are 2-chloro-4-trifluoromethyl-3'-ethoxycarbonylmethylthio-4'-nitrodiphenyl ether, 3-isopropyl-1H-2,1,3-benzothiadiazin-4(3H)-one-2,2-dioxide and salts thereof, 3-isopropyl-1H-pyridino-[3.2-e]-2,1,3-thiadiazin-4(3H)-one-2,2-dioxide and salts thereof, and 1-cyano-8-chloro-3-isopropyl-2,1,3-benzothiadiazin-4(3H)-one-2,2-dioxide.

The ratio of the components to each other may vary widely. The ratio selected depends mainly on the weed spectrum to be combated, and possibly also on the development stage of the plants to be controlled. Advantageously, the ratio of diphenyl ether of the formula I to benzothiadiazinone dioxide of the formula II or pyridinothiadiazinone dioxide of the formula III is from 1:100 to 1:1, preferably from 1:40 to 1:1, parts by weight.

The requisite amount of pure active ingredient—without formulating auxiliaries—in the composition depends on the plants making up the stand, their development stage and the climatic conditions of the location. Generally, application rates are from 0.1 to 5.0 kg of active ingredient composition per hectare.

Crops in which the herbicidal agents according to the invention may be applied to the leaves are essentially those in which their individual components may be used, e.g., cereals, groundnuts, established alfalfa, and numerous other annual or perennial, herbaceous or woody plants.

The application technique is important. The agents according to the invention may be applied before or after the crop and unwanted plants have emerged; post-emergence treatment is preferred. A special application technique is to spray the active ingredients with the aid of spraing equipment in such a way that the leaves of sensitive crop plants are if possible not hit; the active ingredients reach the soil or unwanted plants growing below the crop plants (post-directed, lay-by treatment).

In view of the many application methods possible, the agents according to the invention, or mixtures containing them, may be used in addition to the crop plants listed in the tables in a large number of other crops for eliminating unwanted growth.

The following crop plants are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |

-continued

| Botanical name | Common name |
|---|---|
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* | parsley |
| spp. *tuberosum* | |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | |
| *Ricinus communis* | |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | grain sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

The herbicidal agents according to the invention may be applied for instance on the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol ethoxylated octylphenol and ethoxylated nonylphenol, alkylphenol, polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

Examples of formulations are as follows.

I. 20 parts by weight of a mixture of 1 part by weight of 2-chloro-4-trifluoromethyl-3'-ethoxycarbonylmethylthio-4'-nitrodiphenyl ether and 1 part by weight of 3-isopropyl-1H-2,1,3-benzothiadiazin-4(3H)-one-2,2-dioxide are dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient composition.

II. 20 parts by weight of a mixture of 1 part by weight of 2-chloro-4-trifluoromethyl-3'-ethoxycarbonylmethylthio-4'-nitrodiphenyl ether and 10 parts by weight of 3-isopropyl-1H-2,1,3-benzothiadiazin-4(3H)-one-2,2-dioxide are dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient composition.

III. 3 parts by weight of a mixture of 1 part by weight of 2-chloro-4-trifluoromethyl-3'-ethoxycarbonylmethylthio-4'-nitrodiphenyl ether and 40 parts by weight of the diethanolammonium salt of 3-isopropyl-1H-2,1,3-benzothiadiazin-4(3H)-one-2,2-dioxide are intimately mixed with 97 parts by weight of particulate kaolin. A dust is obtained containing 3% by weight of the active ingredient composition.

IV. 20 parts by weight of a mixture of 1 part by weight of 2-chloro-4-trifluoromethyl-3'-ethoxycarbonylmethylthio-4'-nitrodiphenyl ether and 3 parts by weight of the sodium salt of 3-isopropyl-1H-2,1,3-benzothiadiazin-4(3H)-one-2,2-dioxide are intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 30 parts by weight of a mixture of 1 part by weight of 2-chloro-4-trifluoromethyl-3'-ethoxycarbonylmethylthio-4'-nitrodiphenyl ether and 10 parts by weight of 3-isopropyl-1H-pyridino-[3.2-e]-2,1,3-thiadiazin-4(3H)-one-2,2-dioxide are intimately mixed with a mixture consisting of 92 parts by weight of powdered silica gel and 8 parts by weight of paraffin oil which has been sprayed onto the surface of this silica gel. A formulation of the active ingredient composition is obtained having good adherence.

The new herbicidal agents according to the invention may be mixed and applied together with numerous representatives of other herbicidal or growth-regulating active ingredient groups. Examples of suitable mixture components are diazines, 2,6-dinitroanilines, N-phenylcarbamates, thioloarbamates, halocarboxylic acids, triazines, amides, ureas, triazinones, uraciles, benzofuran derivatives, etc. Such combinations broaden the spectrum of action. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-$\alpha,\alpha,\beta,\beta$-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-3-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
N-(1-ethylpropyl)-2,6-dinitro-3,4-dimethylaniline
N-(1-methylethyl)-N-ethyl-2,6-dinitro-4-trifluoromethylaniline
N-n-propyl-N-$\beta$-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-(3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one 4-isobutylidenamino-6-tert.-butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(2-n-propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
N-2,4-dimethyl-5-(trifluoromethyl)-sulfonylaminophenylacetamide
N-4-methyl-5-(trifluoromethyl)-sulfonylaminophenylacetamide 2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzoisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea 1-(3-chloro-4-methylphenyl)-3,3-dimethylurea
1-(3-chloro-4-methoxyphenyl)-3,3-dimethylurea
1-(3,' dichloro-4-methoxyphenyl)-3,3-dimethylurea
1-[4-(4'-chlorophenoxy)-phenyl]-3,3-dimethylurea
1-[4-(4'-methoxyphenyl)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
2-(2-methylphenoxy-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert-butylamino-4-methoxycarbonyl-5-methylpyrazole.

It may also be useful to apply the mixture according to the invention in admixture with other crop protection agents, e.g., agents for combating pests or phytopathogenic fungi or bacteria. The compounds may also be mixed with solutions of mineral matters used to remedy nutritional or trace element deficiencies. To initiate the herbicidal action, wetting agents, spreader-stickers and non-phytotoxic oils and oil concentrates may be added.

The biological action of the agents according to the invention is illustrated in the following experiments which were carried out in the greenhouse and in the open.

For the greenhouse experiments the vessels used were plastic pots having a volume of 300 cm³ and which were filled with a sandy loam containing about 1.5% humus. The seeds of the test plants were sown shallow, and separately according to species, or pregerminated young plants were used. The plants were treated post-emergence after they had grown to a height of from 3 to 10 cm. The active ingredients were suspended or emulsified in water as vehicle and sprayed through finely distributing nozzles onto the stem parts of the plants and the soil not completely covered by plants. The pots were then set up in different temperature ranges in the greenhouse: heat-loving species at from 20° to 30° C., and those from moderate climates at from 10° to 20° C.

The experiments in the open were run on small plots to which the active ingredients or compositions thereof were applied postemergence (in water as vehicle) with the aid of a plot spray mounted on a tractor.

The following tables contain the compounds tested, the application rates in kg/ha of active ingredient, and the test plant species. Assessments are made on a 0 to 100 scale, 0 denoting no damage or normal emergence, and 100 denoting non-emergence or complete destruction of at least the visible plant parts.

The following active ingredients were employed:
2-chloro-4-trifluoromethyl-3′-ethoxycarbonylmethylthio-4′-nitrodiphenyl ether (active ingredient A),
3-isopropyl-1H-2,1,3-benzothiadiazin-4(3H)-one-2,2-dioxide (active ingredient B), and
3-isopropyl-1H-pyridino-[3.2-e]-2,1,3-thiadiazin-4(3H)-one-2,2-dioxide (active ingredient C).

TABLE 1

List of plant names

| Botanical name | Common name |
| --- | --- |
| Chenopodium album | lambsquarters |
| Matricaria spp. | chamomile |
| Raphanus spp. | wild radish |
| Sinapis spp. | mustard |
| Triticum aestivum | wheat |
| Galium aparine | catchweed bedstraw |
| Stellaria media | chickweed |

TABLE 2

Improvement in herbicidal action and improved crop plant tolerance by a combination of active ingredients A and B; postemergence application in the open

| Active ingredient | Appln. rate [kg/ha] | Test plants and % damage |  |  |  |
| --- | --- | --- | --- | --- | --- |
|  |  | Triticum+ aestivum | Chenopodium album | Matricaria spp. | Raphanus Sinapis spp. |
| A | 0.125 | 8 | 55 | 78 | 72 |
|  | 0.25 | 10 | 65 | 89 | 85 |
| B | 0.75 | 0 | 30 | 73 | 40 |
|  | 1.0 | 0 | 45 | 81 | 50 |
| A + B | 0.125 + 0.75 | 2 | 65 | 98 | 80 |
|  | 0.25 + 0.75 | 5 | 75 | 98 | 90 |

0 = no damage
100 = plants destroyed
+Summer wheat of the "Kolibri" variety

TABLE 3

Synergistic improvement in herbicidal action by employment of compositions of active ingredients A and C; postemergence application in the green house

| Active ingredient | Appln. rate [kg/ha] | Test plants and % damage |  |  |
| --- | --- | --- | --- | --- |
|  |  | Galium aparine | Matricaria spp. | Stellaria media |
| A | 0.03 | 84 | 75 | 75 |
| C | 0.25 | 17 | 49 | 47 |
|  | 0.75 | 30 | 65 | 63 |
| A + C | 0.03 + 0.25 | 98 | 100 | 100 |
|  | 0.03 + 0.75 | 99 | 100 | 100 |

0 = no damage
100 = plants destroyed

I claim:

1. A process for combating the growth of unwanted broadleaf plants which comprises: applying to the unwanted broadleaf plants or to the soil around said plants a herbicidally effective amount of an agent consisting essentially of a diphenyl ether of the formula

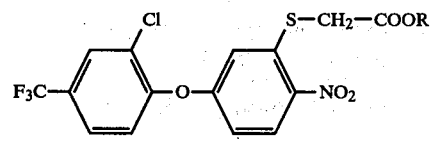

where R is hydrogen, a cation, alkyl or haloalkyl of from 1 to 4 carbon atoms, and a substituted 1H-2,1,3-benzothiadiazin-4(3H)-one-2,2-dioxide of the formula

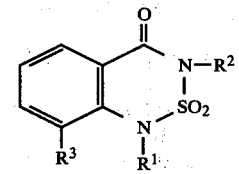

where $R^1$ is hydrogen, a cation, cyano or alkoxyalkyl of from 2 to 4 carbon atoms, $R^2$ is alkyl of from 1 to 4 carbon atoms and $R^3$ is hydrogen, alkyl of from 1 to 4 carbon atoms or halogen, the ratio of I to II being from 1:1 to 1:40 parts by weight and wherein the unwanted plants are found among cereal plants.

2. The process of claim 1, wherein the herbicidal agent is applied to broadleaved weeds, wherein the ratio of I to II of the herbicidal agent is from 1:3 to 1:6, and wherein the unwanted broadleaf plants are found among wheat or barley plants.

3. The process of claim 1, wherein the diphenylether of formula I is 2-chloro-4-trifluoromethyl-3′-ethoxycarbonylmethylthio-4′-nitrodiphenyl ether.

4. The process of claim 3, wherein the compound of the formula II is 3-isopropyl-1H-2,1,3-benzothiadiazin-4(3H)-one-2,2-dioxide or a salt thereof.

* * * * *